(12) United States Patent
Crone et al.

(10) Patent No.: US 11,000,666 B2
(45) Date of Patent: May 11, 2021

(54) BREATHING ASSISTANCE APPARATUS USER INTERFACE

(71) Applicant: Fisher & Paykel Healthcare Limited, Auckland (NZ)

(72) Inventors: Christopher Malcolm Crone, Auckland (NZ); Christopher Simon James Quill, Auckland (NZ); Kevin Peter O'Donnell, Auckland (NZ); Jack Che-Wei Hsu, Auckland (NZ); Jae Chul Han, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 966 days.

(21) Appl. No.: 14/899,500

(22) PCT Filed: Jul. 3, 2014

(86) PCT No.: PCT/NZ2014/000135
§ 371 (c)(1),
(2) Date: Dec. 17, 2015

(87) PCT Pub. No.: WO2015/002550
PCT Pub. Date: Jan. 8, 2015

(65) Prior Publication Data
US 2016/0144148 A1 May 26, 2016

Related U.S. Application Data

(60) Provisional application No. 61/842,917, filed on Jul. 3, 2013.

(51) Int. Cl.
*A61M 16/16* (2006.01)
*G16H 40/63* (2018.01)
(Continued)

(52) U.S. Cl.
CPC ........ *A61M 16/16* (2013.01); *A61M 16/0051* (2013.01); *A61M 16/0057* (2013.01);
(Continued)

(58) Field of Classification Search
CPC .............. A61M 16/16; A61M 16/0051; A61M 16/109; A61M 16/06; A61M 16/0057; A61M 16/021; G06F 19/00; G16H 40/63
See application file for complete search history.

(56) References Cited

U.S. PATENT DOCUMENTS 4,550,726 A 11/1985 McEwen
5,237,987 A 8/1993 Anderson et al.
(Continued)

FOREIGN PATENT DOCUMENTS

WO WO 2011/056080 A1 5/2011
WO WO 2011/085179 A1 7/2011
WO WO 2013/151448 A2 10/2013

OTHER PUBLICATIONS

International Search Report; PCT/NZ2014/000135; dated Sep. 14, 2014; 3 pages.
(Continued)

*Primary Examiner* — Margaret M Luarca
(74) *Attorney, Agent, or Firm* — Knobbe, Martens, Olson & Bear, LLP

(57) ABSTRACT

A breathing assistance apparatus user interface is described which presents animated information related to the management of the apparatus. The user interface is provided on a display screen of the apparatus. The animated illustrations can correspond to operational modes, warnings, user instructions, fault conditions, status, menu options, and the like. The animations can include a sequence of images shown in rapid succession which depict moving icons or objects, scrolling text, flashing colors, or any combination of these or
(Continued)

the like. The user interface can combine static information along with animations.

16 Claims, 4 Drawing Sheets

(51) Int. Cl.
    *A61M 16/00*     (2006.01)
    *G06F 19/00*     (2018.01)
    *A61M 16/10*     (2006.01)
    *A61M 16/06*     (2006.01)

(52) U.S. Cl.
    CPC .......... *A61M 16/021* (2017.08); *A61M 16/06* (2013.01); *A61M 16/109* (2014.02); *G06F 19/00* (2013.01); *G16H 40/63* (2018.01); *A61M 2205/33* (2013.01); *A61M 2205/505* (2013.01)

(56) References Cited

U.S. PATENT DOCUMENTS

| | | | |
|---|---|---|---|
| 7,455,240 B2 * | 11/2008 | Chapman, Jr. | .......... F23N 5/022 |
| | | | 236/91 D |
| 8,160,725 B2 | 4/2012 | Allgaier | |
| 8,851,068 B2 | 10/2014 | Cohen et al. | |
| 2003/0135087 A1 * | 7/2003 | Hickle | ................ G06F 19/3456 |
| | | | 600/26 |
| 2006/0290525 A1 | 12/2006 | Andersen et al. | |
| 2007/0144516 A1 * | 6/2007 | Doyle | ............... A61M 16/0883 |
| | | | 128/204.18 |
| 2008/0092891 A1 * | 4/2008 | Cewers | ................. A61M 16/12 |
| | | | 128/204.18 |
| 2009/0024008 A1 * | 1/2009 | Brunner | ............ A61M 16/0051 |
| | | | 600/301 |
| 2009/0090363 A1 | 4/2009 | Niland et al. | |
| 2010/0065054 A1 | 3/2010 | Bowman et al. | |
| 2010/0069725 A1 * | 3/2010 | Al-Ali | .................. A61B 5/0205 |
| | | | 600/301 |
| 2010/0132708 A1 * | 6/2010 | Martin | .............. A61M 16/1075 |
| | | | 128/204.17 |
| 2010/0152554 A1 * | 6/2010 | Steine | ................ A61B 5/14532 |
| | | | 600/309 |
| 2011/0162647 A1 | 7/2011 | Huby et al. | |
| 2011/0271960 A1 * | 11/2011 | Milne | .................... G16H 15/00 |
| | | | 128/205.23 |
| 2012/0272955 A1 * | 11/2012 | Cool | ...................... A61B 7/003 |
| | | | 128/203.12 |
| 2013/0125883 A1 * | 5/2013 | Bonassa | ............ A61M 16/0057 |
| | | | 128/202.22 |

OTHER PUBLICATIONS

Written Opinion of the ISA; PCT/NZ2014/000135; dated Sep. 14, 2014; 8 pages.

* cited by examiner

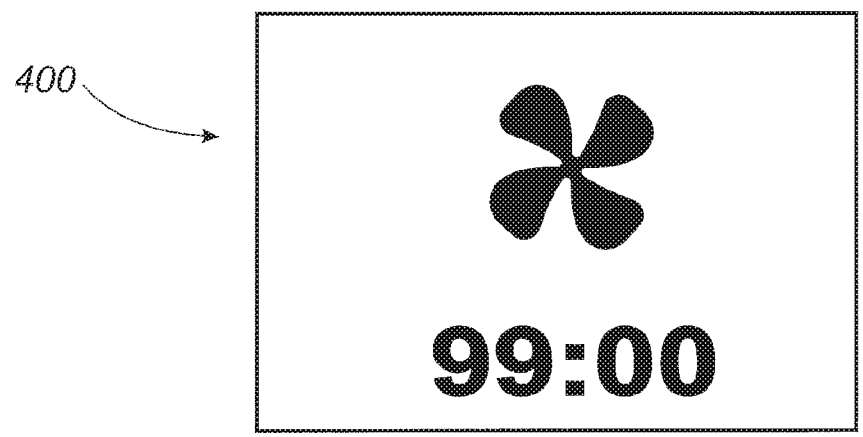
405a → Do not wear inte
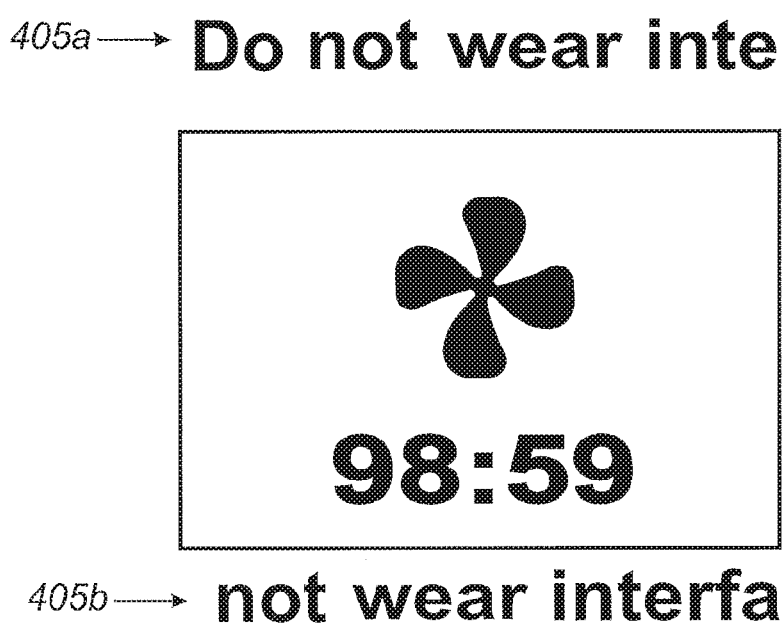
405b → not wear interfa
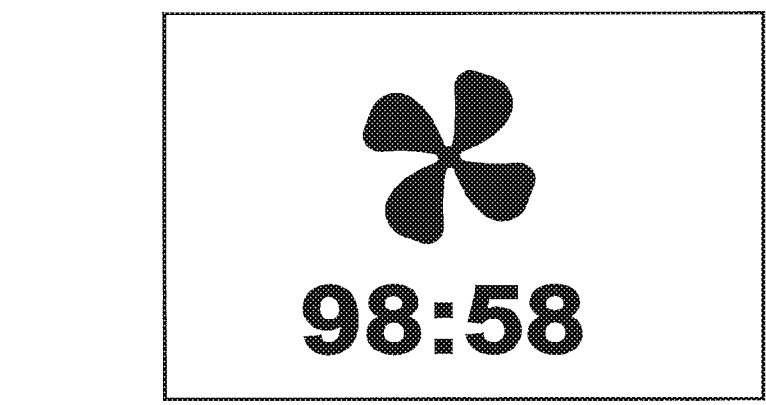
FIG. 4  405c → wear interface du

BREATHING ASSISTANCE APPARATUS USER INTERFACE

BACKGROUND

Field

The present disclosure relates generally to a user interface for a breathing assistance apparatus and more particularly to animated graphics used to convey information to a user of a breathing assistance apparatus.

Description of Related Art

A variety of machines can be used to assist with the breathing of a patient. Some of these machines are used among a plurality of users and are used almost continuously. Some of the machines are used by very few users and are used intermittently. These machines can deliver a heated and/or humidified flow of breathing gases to the user.

The machines may be operated by individuals and trained health professionals. Configuration and management of these machines can be difficult and time consuming. The machine may have multiple modes of operation and multiple operating conditions or events that require action of a user. In some instances, such conditions may be indicated by a numerical fault code, requiring the user or operator to consult a look-up table or call a technician. In some instances, it may be difficult to quickly assess the operating modes and conditions of the machine to efficiently manage the machine.

SUMMARY

The invention broadly relates to a breathing assistance apparatus comprising: a flow generator operable to generate a flow of breathable gas; a humidifier chamber connected to the flow generator that is operable to heat and humidify the flow of breathable gas; a conduit connected to receive the heated and humidified flow of breathable gas from the humidification chamber; a user breathing interface connected to the conduit for delivering the heated and humidified flow of breathable gas to a user; a controller operable to control the apparatus; a user control interface operatively connected to the controller that is operable by a user to control the apparatus; and a display screen adapted to provide visual information to a user, wherein the display screen is configured to display an animation of a rolling cart when the breathing assistance apparatus is operated in a transport mode in which the apparatus is configured to reduce power usage relative to a normal mode.

In an embodiment, the controller is configured to operate the apparatus to generate the flow of heated and humidified gas at a lower temperature when operating in transport mode, relative to when operating in the normal mode.

In an embodiment, the controller is configured to automatically cause the apparatus to enter the transport mode upon the controller detecting the apparatus being connected to a universal power supply rather than an electrical wall socket.

In one embodiment, the controller comprises a countdown timer with a configurable preset time, the countdown timer being triggered upon entering transport mode, and the controller automatically causing the apparatus to revert to the normal mode at the expiration of the preset time. In another embodiment, the controller comprises a countdown timer with a configurable preset time, the countdown timer being triggered upon entering transport mode, and the controller automatically causing the apparatus to revert to the mode of operating it was in prior to entering the transport mode at the expiration of the preset time.

In an embodiment, the animation of the rolling cart comprises a series of images shown in succession to display an animated cart moving across a portion of the display screen.

In an embodiment, the apparatus is configured to display the animation of the rolling cart on a portion of the display screen while maintaining another portion of the display screen unchanged.

In an embodiment, the controller is configured to change the display of the animation of the rolling cart to a different animation upon the controller detecting a triggering event. In one example, the triggering event is exiting the transport mode. In one configuration, the controller is configured to maintain another portion of the display screen displaying static information unchanged while changing to a different animation.

Also described is a breathing assistance apparatus comprising: a flow generator operable to generate a flow of breathable gas; a humidifier chamber connected to the flow generator that is operable to heat and humidify the flow of breathable gas; a conduit connected to receive the heated and humidified flow of breathable gas from the humidification chamber; a user breathing interface connected to the conduit for delivering the heated and humidified flow of breathable gas to a user; a controller operable to control the apparatus; a user control interface operatively connected to the controller that is operable by a user to control the apparatus; and a display screen adapted to provide visual information to a user, wherein the display screen is configured to provide scrolling text across a first portion of the display screen to provide textual information related to static information displayed on a second portion of the display screen.

In an embodiment, the scrolling text comprises a series of images shown in succession to display text scrolling or moving across a portion of the display screen.

In an embodiment, text of the scrolling text is surrounded by a coloured background. In one example, the colour of the text and surrounding background of the scrolling text are different to create a high contrast. In one configuration, the colour of the text or surrounding background of the scrolling text is substantially the same as the colour of at least some of the static information displayed in the second portion of the display screen.

In an embodiment, the scrolling text comprises flashing colours or text indicative of an urgent message or alarm.

In an embodiment, the apparatus further comprises an operable audio output, and wherein the controller is configured to play audio over the audio output that is associated with the scrolling text. In one example, the audio is an audio cue or audio instructions that correspond to the scrolling text.

In an embodiment, the controller is configured to change either of the first or second portions of the screen in response to user input or a triggering event, while maintaining the other of the first or second portions of the screen unchanged. In one example, the controller is configured to change the text information of the scrolling text in the first portion of the display screen in response to user input or a triggering event, while the static information in the second portion of the display screen is unchanged or unaffected by the change to the scrolling text. In another example, the controller is configured to change the static information displayed in the second portion of the display screen in response to user input or a triggering event, while the text information of the scrolling text in the first portion of the display screen is unchanged or unaffected by the change in the static information.

In an embodiment, the static information displayed in the second portion of the display screen comprises icons or readings indicative of apparatus operating parameters.

In an embodiment, the first portion of the display screen is at the bottom of the display screen such that the scrolling text is displayed across the bottom of the display screen.

In an embodiment, the apparatus is configured to display the textual information of the scrolling text in a plurality of languages in succession.

In an embodiment, the apparatus is configured to display the scrolling text in the first portion of the display screen for a limited duration.

Also described is a breathing assistance apparatus comprising: a flow generator operable to generate a flow of breathable gas; a humidifier chamber connected to the flow generator that is operable to heat and humidify the flow of breathable gas; a conduit connected to receive the heated and humidified flow of breathable gas from the humidification chamber; a user breathing interface connected to the conduit for delivering the heated and humidified flow of breathable gas to a user; a controller operable to control the apparatus; a user control interface operatively connected to the controller that is operable by a user to control the apparatus; and a display screen adapted to provide visual information to a user, wherein the display screen is configured to provide scrolling text across a first portion of the display screen and to provide animations on a second portion of the display screen.

In an embodiment, the scrolling text comprises a series of images shown in succession to display text scrolling or moving across a portion of the display screen.

In an embodiment, the text of the scrolling text is surrounded by a coloured background. In one example, the colour of the text and surrounding background of the scrolling text are different to create a high contrast. In one configuration, the colour of the text or surrounding background of the scrolling text is substantially the same as the colour of at least one of the animations displayed in the second portion of the display screen.

In an embodiment, the scrolling text comprises flashing colours or text indicative of an urgent message or alarm.

In an embodiment, the apparatus further comprises an operable audio output, and wherein the controller is configured to play audio over the audio output that is associated with the scrolling text. In one configuration, the audio is an audio cue or audio instructions that correspond to the scrolling text.

In an embodiment, the controller is configured to change either of the first or second portions of the screen in response to user input or a triggering event, while maintaining the other of the first or second portions of the screen unchanged. In one configuration, the controller is configured to change the text information of the scrolling text in the first portion of the display screen in response to user input or a triggering event, while the animations in the second portion of the display screen is unchanged or unaffected by the change to the scrolling text. In another configuration, the controller is configured to change the animations displayed in the second portion of the display screen in response to user input or a triggering event, while the text information of the scrolling text in the first portion of the display screen is unchanged or unaffected by the change in the animations.

In an embodiment, the animations displayed in the second portion of the display screen comprise information indicative of any one or more of: apparatus operating parameters, settings, and/or conditions.

In an embodiment, the controller is configured to change the animations displayed in the second portion of the display screen in response to any one or more of the following: operating parameters measured by the apparatus, changes in operational modes, user input, and/or triggering events.

In an embodiment, the animations displayed in the second portion of the display screen comprise an animated fan, timer, or both.

In an embodiment, the first portion of the display screen is at the bottom of the display screen such that the scrolling text is displayed across the bottom of the display screen.

In an embodiment, the scrolling text comprises text information indicative of any one or more of the following: warnings, instructions, operational parameters, preventative warning information, fault and/or conditions.

A breathing apparatus is described which comprises a display for illustrating or presenting animated information related to the management of the apparatus. The display can be configured to display animated illustrations corresponding to operational modes, warnings, user instructions, fault conditions, status, menu options, and the like. The animations can include a sequence of images shown in rapid succession which depict moving icons or objects, scrolling text, flashing colors, or any combination of these or the like. In some embodiments, the display can show static information along with animations.

Also described is a breathing assistance apparatus is provided that includes a display screen configured to provide visual information to a user. The apparatus can be advantageously configured to provide the display screen with a series of images depicting an appropriate animation when in a particular mode. In some embodiments, the display screen displays a series of images depicting the movement of a rolling cart when in a transport mode.

Also described is a breathing assistance apparatus is provided that includes a display screen configured to provide visual information to a user. The apparatus can be advantageously configured to provide text information to a user on the display screen. The apparatus can be configured to display the text information as scrolling text. In some embodiments, the text information to be displayed on the display screen is selected based on an operation mode, a fault condition, an event, or the like. In some embodiments, the text information is displayed as scrolling text when the text information does not fit across the display screen and as static text when it fits across the display screen.

Also described is a breathing assistance apparatus is provided that includes a flow generator, a humidifier chamber connected to the flow generator, a conduit connected to the flow generator, a user breathing interface connected to the conduit, and a display screen adapted to provide visual information to a user. The apparatus can advantageously be configured to monitor one or more characteristics of use; and, upon an occurrence of a triggering event, to provide a series of image frames to the display. The series of image frames can depict an animated action that is configured to instruct a user to make an adjustment to the apparatus based upon the animated action to address the occurrence of the triggering event. The series of image frames can depict scrolling text providing instructions, warnings, fault conditions, or the like to a user.

Also described is a breathing assistance apparatus comprising: a display screen adapted to provide visual information to a user, wherein the display screen is configured to display an animation of a rolling cart to indicate a transport mode.

Also described is a breathing assistance apparatus comprising: a flow generator; a humidifier chamber connected to the flow generator; a conduit connected to the flow generator; a user breathing interface connected to the conduit; and a display screen adapted to provide visual information to a user, wherein the display screen is configured to display an animation of a rolling cart when the breathing assistance apparatus is put into a low power mode for transport.

Also described is a breathing assistance apparatus comprising: a flow generator; a humidifier chamber connected to the flow generator; a conduit connected to the flow generator; a user breathing interface connected to the conduit; and a display screen adapted to provide visual information to a user, wherein the display screen is configured to provide scrolling text across a first portion of the display screen to provide textual information related to static information displayed on a second portion of the display screen.

Also described is a breathing assistance apparatus comprising: a flow generator; a humidifier chamber connected to the flow generator; a conduit connected to the flow generator; a user breathing interface connected to the conduit; and a display screen adapted to provide visual information to a user, wherein the display screen is configured to provide scrolling text across a first portion of the display screen and to provide animations on a second portion of the display screen.

BRIEF DESCRIPTION OF THE DRAWINGS

These and other features, aspects, and advantages will now be described with reference to the drawings of some embodiments, which embodiments are intended to illustrate and not to limit the scope of the disclosure, and in which figures:

FIG. 4 illustrates an example of a series of images used in an animation showing a breathing apparatus display providing information to a user as scrolling text across the display in conjunction with dynamic information and other animations.

DETAILED DESCRIPTION

A breathing assistance apparatus can include a number of elements that work to provide gases to a user. To assist a user in operating the breathing apparatus, it can include a display screen with an accompanying display interface that provides information to a user in the form of text, images, animations, colors, icons, and the like. The display screen can be configured to display static images, semi-static images (e.g., sensor readouts) and animated images on the screen at the same time. The display screen can be configured to update the displayed information in real time and in response to changing operating conditions, fault conditions, user selections (e.g., using a menu of the user interface), events, and the like.

In some embodiments, the breathing assistance apparatus monitors one or more characteristic of use and, upon a triggering event occurring, the apparatus provides a series of image frames such as, for example, graphics, recorded images, visual descriptions, visual directions, still images, and/or videos to the display. The series of image frames depict one or more still graphics and/or animated actions such that the user can make an adjustment to the apparatus based upon the image frames to address the occurrence of the triggering event.

Figure 1:
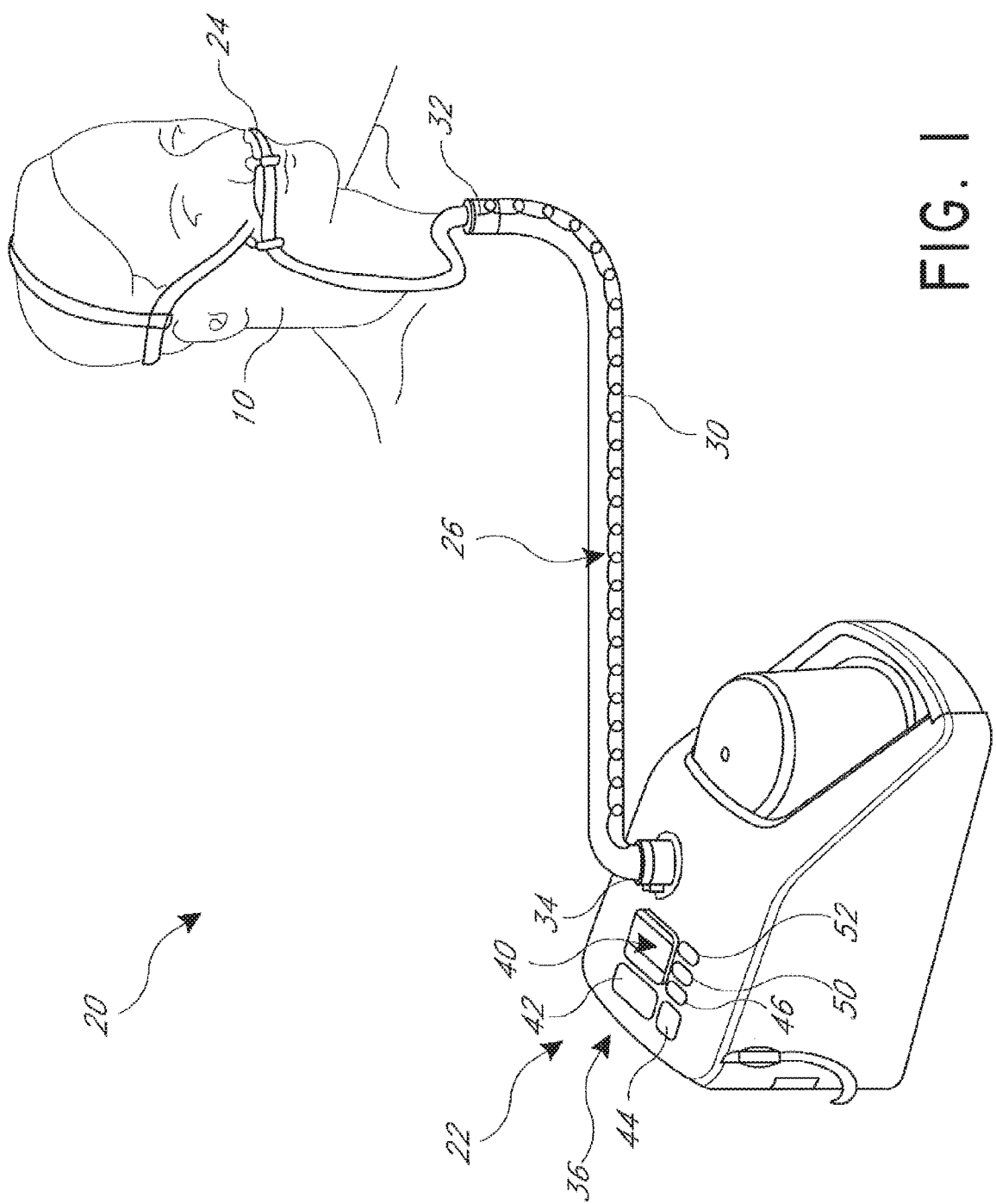
FIG. 1 is a perspective view of an example breathing assistance apparatus that provides a humidified and heated flow of fluid to a user or patient.

FIG. 1 illustrates an example breathing assistance apparatus 20 that provides a humidified and heated flow of fluid to a user or patient 10. The illustrated apparatus 20 comprises a high-flow breathing assistance apparatus; however, features, aspects, and advantages of some embodiments can be used with other types of apparatus used to supply a humidified and/or heated flow of fluid (e.g., gases or air) to the user or patient 10. For example, features, aspects, and advantages of some embodiments can be used with CPAP machines, insufflation humidifiers for laparoscopic or other surgical procedures, respiratory humidifiers, humidifiers for noninvasive ventilation applications, humidifiers for invasive ventilation applications, infant resuscitation devices, and the like. Embodiments described herein can be used with the breathing assistance apparatus and display interface described in international PCT patent application publication WO2013/151448, which is incorporated by reference in its entirety so as to form a part of this specification.

In some embodiments, the apparatus 20 can include a display 40 configured to display a series of images in succession that illustrate an animation and/or scrolling text. The animation and/or scrolling text can be used to instruct a user on how to perform a particular action, to provide information regarding the apparatus 20 to the user, or to provide an indication of an operational mode of the apparatus 20 to the user. The series of images can be displayed in response to a triggering event and the animated action can be configured to present one or more methods of responding to the triggering event. The apparatus 20 can be configured to detect various triggering events and to automatically display a corresponding series of images. For example, the apparatus 20 can be configured to detect a fault condition. In response, the apparatus 20 can display a scrolling text instructing the user how to correct the fault condition.

In some embodiments, the series of images displayed on the display 40 can include flashing lights, coloring, shading, or other similar visual cues to correlate the animation or scrolling text to relevant information displayed on the display 40. For example, the scrolling text can have a colored background that is the same or nearly the same as an icon on the display or other information on the display to which the scrolling text applies. In some embodiments, no words are used such that the visual images can communicate an operational mode, fault condition, or the like to any user independent of language or technical background. In some embodiments, audible cues or instructions can be provided in addition to the animations and/or scrolling text.

With continued reference to FIG. 1, the apparatus 20 comprises a flow generating apparatus 22. The illustrated flow generating apparatus 22 can be connected to a patient interface 24 with a flexible conduit 26. The patient interface 24 can be any suitable patient interface. For example, but without limitation, the patient interface 24 can comprise noninvasive interfaces including, but not limited to, adult nasal cannula, infant nasal cannula, full face masks, combination oral/nasal masks, nasal masks, nasal pillows, high flow cannula, or the like. In some configurations, the patient interface 24 can comprise invasive or minimally invasive interfaces including, but not limited to, endotracheal tubes, insufflation devices, or the like. In some configurations, adaptors and connectors can be provided for coupling to tracheotomy devices and masks.

In the illustrated configuration, the flexible conduit 26 can comprise a heating element 30 and a sensing element 32. In some configurations, the sensing element 32 can be positioned at an end portion of the flexible conduit 26 closest to the patient interface 24. In some configurations, the sensing element 32 is positioned within the lumen defined by the flexible conduit 26 such that the sensing element 32 is exposed to the fluid being carried within the lumen. The sensing element 32 can sense a characteristic or attribute of the fluid being carried within the lumen. In some configurations, the sensing element 32 is arranged and configured to sense the temperature of the fluid passing through the lumen.

The end of the flexible conduit 26 closest to the flow generating apparatus 22 comprises a connector 34. The connector 34 can be configured to establish both a pneumatic connection between the flow generating apparatus 22 and the lumen of the flexible conduit 26 and an electrical connection between at least the heating element 30 of the flexible conduit 26 and the flow generating apparatus 22. In some configurations, the connector 34 facilitates establishing both the pneumatic connection and the electrical connection in a single step.

With continued reference to FIG. 1, the flow generating apparatus 22 comprises a user control interface 36. The user control interface 36 enables interaction between the user, patient 10, or another person (e.g., without limitation, health professionals, distributors, or the like) and the flow generating apparatus 22. The illustrated user control interface 36 comprises a display screen 40. The display screen 40 can be any suitable display screen. In some configurations, the display screen 40 comprises an organic light-emitting diode (OLED) screen. In some configurations, the display screen 40 can comprise a full color display with a pixel count of between about 6,000 pixels and about 500,000 pixels. In some configurations, the display screen 40 can comprise a pixel count of about 20,480 pixels. In some configurations, the display screen can comprise a screen size of about 128 pixels by about 160 pixels (vertical by horizontal). In some configurations, the display screen can be about 1.8 inches diagonally to about 4 inches diagonally. To reduce heat transferred from the screen to other components of the apparatus 22, the screen can be run with a black screen (e.g., most of the pixels are inactive during operation of the apparatus 22).

The illustrated user interface 36 comprises a power key/button 42, a mute key/button 44, an up arrow key/button 46, a down arrow key/button 50 and a mode key/button 52. In some configurations, the user interface 36 can include some combination of mechanical keys, electro-mechanical keys, and touch-sensitive capabilities such as where the display 40 comprises a touch-screen and navigation through a menu structure or other suitable manner of device operation can be provided via the display 40. In some configurations, a joystick, a toggle, or the like can be provided for navigation through a menu structure or other suitable manner of device operation.

The apparatus 22 also comprises a suitable controller, which includes memory and other components used for sensing various characteristics of flows and operation of the apparatus. Moreover, the apparatus 22 can comprise a speaker or other audible alert generator.

Example User Interface Animations

Figure 2:
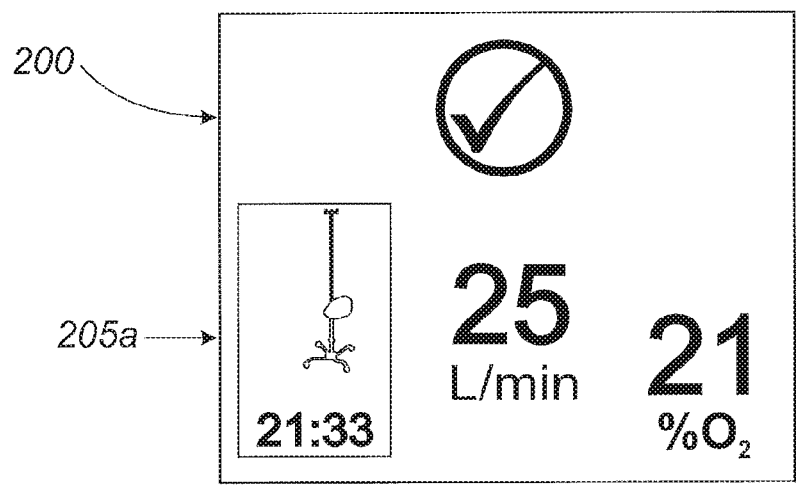
FIG. 2 illustrates an example of a series of images used in an animation showing a breathing apparatus display operating in a transport mode.
Figure 2:
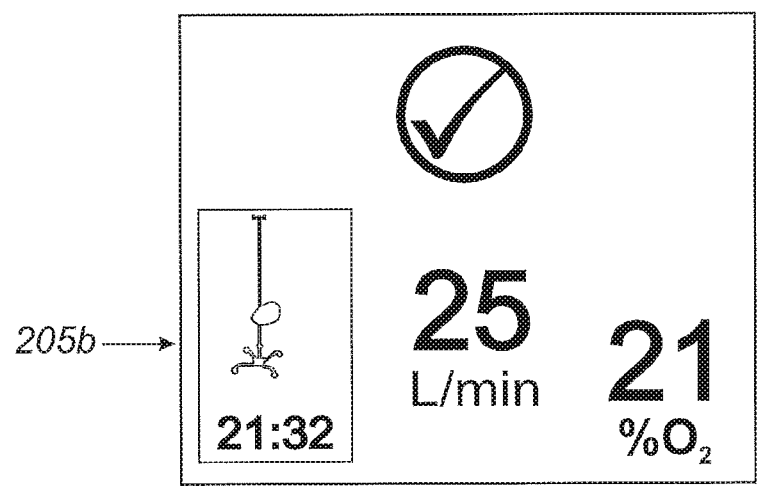
Figure 2:
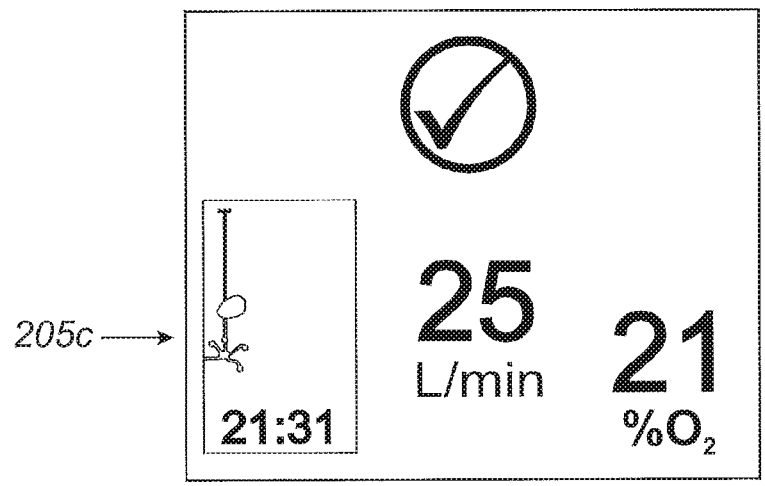

FIG. 2 illustrates an example of a series of images used in an animation showing a breathing apparatus display operating in a transport mode. The breathing apparatus display can include a display 200 that provides information relevant to the operation of the breathing assistance apparatus. A portion of the display 200 can be used to provide an animation. For example, FIG. 2 illustrates a sequence of images that shows an animated cart 205a, 205b, 205c, moving across a portion of the screen. When shown in succession, it appears as though the cart is moving. In addition, a timer is displayed in the animation region. The animation can be configured to convey to a user that the apparatus 22 is being operated in a transport mode. This can be done, as shown, using a moving element associated with the apparatus, such as the rolling cart. In some embodiments, other animations can be used which convey to a user that the apparatus is in a transport mode such as, for example, a car, traffic signals, a dynamic arrow, flashing indicator, or the like. In some embodiments, scrolling text can be used to indicate that the apparatus is in a transport mode.

The breathing assistance apparatus can be used in a transport mode. For example, in the transport mode the output gas temperature setting can be reduced (e.g., typically to about 31 C from about 37 C in the normal mode). In some embodiments, entering the transport mode can cause the apparatus 22 to reduce or minimize power usage by the heater plate, motors, and the like. The reduction or minimization of power can be done to reduce power consumption when connected to a universal power supply ("UPS") for transportation from one location to another when the apparatus cannot or will not be plugged into an electrical socket. When in transport mode, the apparatus 22 can have a countdown timer with a preset period of time (e.g., about 30 minutes), after the expiration of which the apparatus 22 automatically reverts to a normal mode of operation. The screen can display the temperature setting and the countdown timer indicating when the apparatus will automatically revert to a normal mode of operation. In some embodiments, the countdown timer can be reset by the user if the transportation will last longer than the timer provides. In some embodiments, the apparatus reverts to the mode of operation it was in prior to being put into the transportation mode. In some embodiments, the transportation mode screen can display other information or indicators, such as a flow rate, an oxygen setting, a youth-sub mode, or the like.

In some embodiments, the apparatus 22 can be configured to enter transport mode when connected to a UPS. The apparatus 22 can be configured to understand and communicate appropriate handshake protocols with UPS systems so as to recognize when it is connected to a UPS rather than an electrical wall socket. In some embodiments, the apparatus 22 can remain in transport mode until disconnected from the UPS and/or connected to an electrical wall socket.

The display 200 can be configured to change only a portion of the screen while maintaining another portion unchanged. For example, the animations can change when the apparatus detects a triggering event, such as the end of a transport mode of operation. When the animation changes, the static information can remain unchanged and/or unaffected by the change to the animations.

Figure 3:
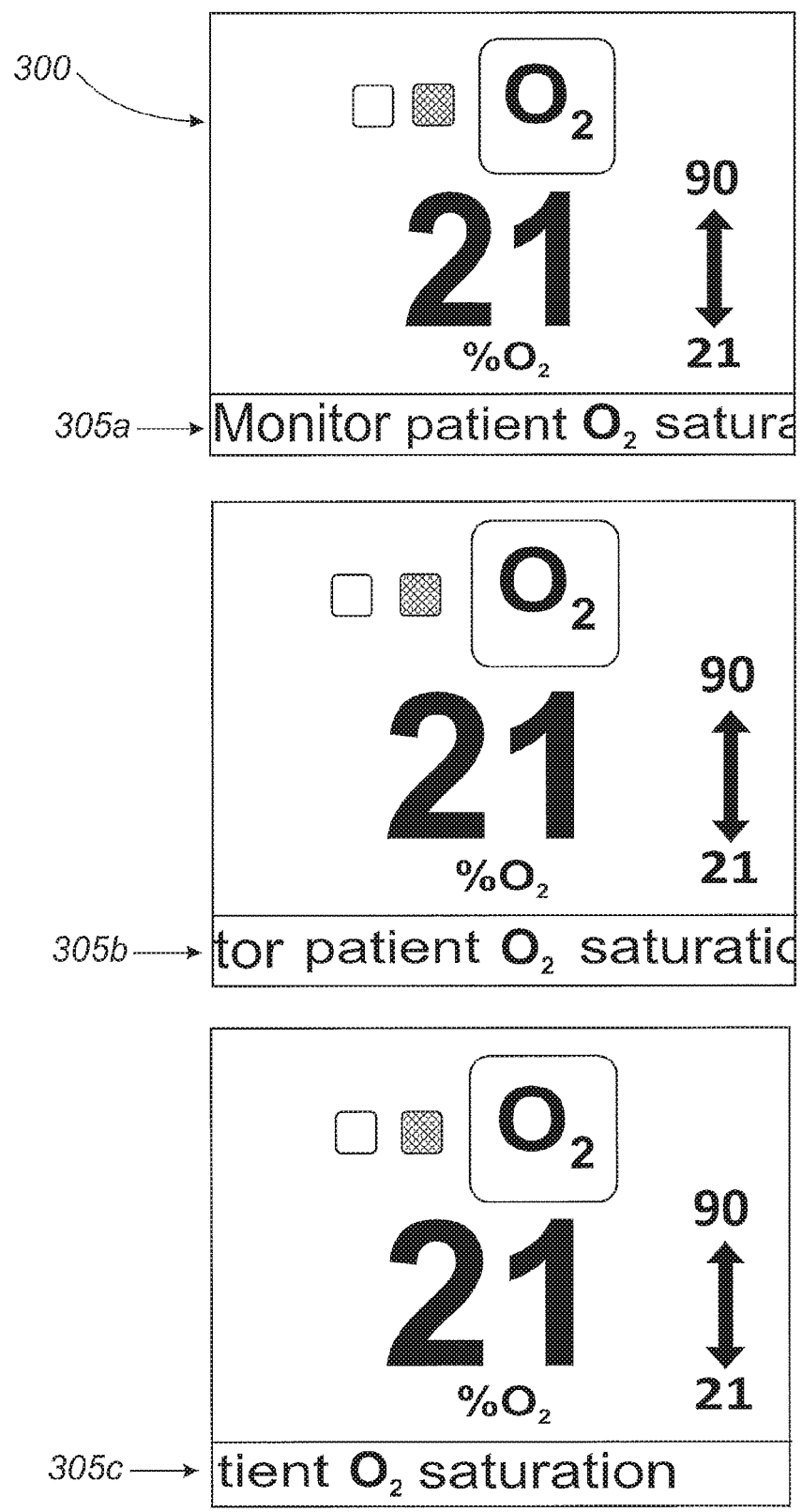
FIG. 3 illustrates an example of a series of images used in an animation showing a breathing apparatus display providing instructions to a user as scrolling text across the display in conjunction with other information.

FIG. 3 illustrates an example of a series of images used in an animation showing a breathing apparatus display providing instructions to a user as scrolling text across the display in conjunction with static information. The breathing apparatus display can include a display 300 that provides information relevant to the operation of the breathing assistance apparatus. A portion of the display 300 can be used to provide scrolling text. For example, FIG. 3 illustrates a sequence of images that shows scrolling text 305*a*, 305*b*, 305*c*, moving across a bottom portion of the screen. When shown in succession, it appears as though the text is moving or scrolling across a portion of the screen. The text of the scrolling text can be surrounded by a colored region, or a banner. The colors of the text and banner can be different and can have a high contrast to facilitate reading. In addition, static information is displayed on the display 300, including icons, oxygen saturation value readings, oxygen saturation ranges, or the like. The scrolling text can be configured to convey instructions to a user, including to "Monitor patient $O_2$ saturation," as illustrated. The scrolling text can include a background color or a font color that is the same or similar to the general color of the information being presented (e.g., the oxygen saturation value), the background or foreground of an icon (e.g., the "$O_2$" icon), or other such information presented on the display 300. Other icons, measurements, ranges, and the like can be used in the display 300, such as flow rate readings, timers, operational mode indicators, menus, and the like. In some embodiments, the scrolling text can include flashing colors or text to indicate an urgent message or an alarm. In some embodiments, an audible cue can be played with the scrolling text and/or audible instructions can be provided which correspond to the scrolling text. For example, a melody or chime can be played in conjunction with an animation or scrolling text associated with a warning. Audible cues can be different for different animations and/or scrolling text messages.

The static information in FIG. 3 can be static relative to the dynamic information being presented as scrolling text or animations. The static information can be configured to change according to readings or values measured by the apparatus, or other events. In some embodiments, the display 300 can change according to user input, triggering events, and the like. The display 300 can be configured to change only a portion of the screen while maintaining another portion unchanged. For example, the scrolling text can change when the apparatus detects a triggering event. When the scrolling text changes, the static information can remain unchanged and/or unaffected by the change to the scrolling text. Similarly, the scrolling text can continue to present the same text information when the display 300 changes what is being displayed, such as changing from an oxygen saturation reading to a flow rate reading. As another example, when the display interface provides a menu to the user, the scrolling text can remain scrolling across the bottom of the page or the menu can occupy the entire display 300.

FIG. 4 illustrates an example of a series of images used in an animation showing a breathing apparatus display providing information to a user as scrolling text across the display in conjunction with dynamic information and other animations. The breathing apparatus display can include a display 400 that provides information relevant to the operation of the breathing assistance apparatus. A portion of the display 400 can be used to provide scrolling text. For example, FIG. 4 illustrates a sequence of images that shows scrolling text 405*a*, 405*b*, 405*c*, moving across a bottom portion of the screen. When shown in succession, it appears as though the text is moving or scrolling across a portion of the screen. In addition, other dynamic information and animations are displayed on the display 400, including a timer and an animated fan. The scrolling text can be configured to convey instructions to a user that are related to the animated information being displayed, including to "Do not wear interface during . . . ," as illustrated. The scrolling text can include a background color or a font color that is the same or similar to the general color of the information being presented (e.g., the fan and timer), or other such information presented on the display 400. In some embodiments, the scrolling text can include flashing colors or text to indicate an urgent message or an alarm. In some embodiments, an audible cue can be played with the scrolling text and/or audible instructions can be provided which correspond to the scrolling text.

The animations in FIG. 4 can be configured to change without affecting the scrolling text in the display 400. The animations can be configured to change according to readings or values measured by the apparatus, changes in operational modes, or other events. In some embodiments, the display 400 can change according to user input, triggering events, and the like. The display 400 can be configured to change only a portion of the screen while maintaining another portion unchanged. For example, the scrolling text can change when the apparatus detects a triggering event. When the scrolling text changes, the animations can remain unchanged and/or unaffected by the change to the scrolling text. Similarly, the scrolling text can continue to present the same text information when the display 400 changes the animations being displayed, such as changing from transport mode to normal operation. As another example, when the display interface provides a menu to the user, the scrolling text can remain scrolling across the bottom of the page or the menu can occupy the entire display 400.

In the displays 300 and 400 of FIGS. 3 and 4, respectively, scrolling text can provide warnings, instructions, operational parameters, preventive warning information, fault conditions, and the like to a user. Examples of such information can include, without limitation, replacing a filter of the apparatus, detecting a disconnection from the conduit heater wire, detecting a loss of resistance to flow, indicating a possible leak, connection of the youth sub-mode cannula, detecting a higher than expected resistance to flow, unkinking a hose, determining if the youth sub-mode interface is installed, unclogging a nasal cannula, detecting oxygen content above or below a set level, detecting a water level to be low or empty, detecting an oxygen supply during a disinfection mode, detecting an interruption in the oxygen supply, detecting a prolonged stoppage of user breathing, detecting a user breathing rate that exceeds a limit, and the like. Thus, in some configurations, the apparatus 22 is configured to prompt users to perform maintenance tasks and troubleshooting through the use of animations, scrolling text, or other graphical displays.

Preferably, the apparatus 22 is capable of displaying the scrolling text in any of a plurality of languages, which can be set by the user. In some embodiments, the scrolling text can be presented in multiple languages in succession. For example, the scrolling message can be displayed first in English, then in Spanish, then in French, or any other language and in any order. This can be advantageous in that it reduces or eliminates the need for creating or providing a user manual in multiple languages.

In some embodiments, the letters of the scrolling text can be the same color as the background of the display screen or display interface. In some embodiments, the banner around the scrolling text can be the same color as the background of the display screen or display interface. The text can be a bright color to contrast with the background and/or banner.

Similarly, in some embodiments the banner can be a bright color to contrast with the background and/or text.

In some embodiments, the scrolling message can be shown for a limited duration. The limited duration can be based on an amount of time being displayed or a number of times the full message is displayed on the display interface. For example, the scrolling message can be configured to be displayed 3 times. Other numbers can be used as well, including 1 time, 2 times, 4 times, 5 times, 6 times, etc. As another example, the scrolling message can be configured to be displayed for 5 seconds, 10 seconds, 30 seconds, 1 minute, 2 minutes, etc.

Although the disclosure herein has been presented in terms of some embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice embodiments encompassed by this disclosure. Accordingly, the scope of each of the claimed inventions is intended to be defined only by the claims that follow.

What is claimed is:

1. A breathing assistance apparatus comprising:
a single housing including a flow generator and a humidifier disposed within the single housing;
a controller operable to control at least one aspect of operation of the breathing assistance apparatus;
a user control interface operatively connected to the controller that is operable by a user to control the at least one aspect of the breathing assistance apparatus;
an organic light emitting diode display screen adapted to provide visual information regarding the breathing assistance apparatus to a user, the display screen comprising a first portion, a second portion, and a third portion, the first portion of the display screen configured to display scrolling text along the lower portion of the display screen, the second portion of the display screen configured to display dynamic information comprising a countdown timer, and a third portion of the display configured to display an animation comprising a moving icon indicative of an operational mode that visually illustrates to a user that the operational mode is active, wherein during the operational mode, the scrolling text provides textual information that is related to the animation while the moving icon moves but remains unchanged and the countdown timer counts down, the scrolling text being displayable in conjunction with the animation, wherein the scrolling text is indicative of instructions, a warning, a fault condition or an event of the breathing assistance apparatus,
where the user control interface and the display screen are located on an upper side of the single housing during operation of the breathing assistance apparatus wherein the breathing assistance apparatus comprises multiple modes of operation including a disinfection mode.

2. The breathing assistance apparatus of claim 1, further comprising an inspiratory conduit and a user breathing interface, the inspiratory conduit being in fluid communication with the humidifier and the user breathing interface such that the flow of breathing gases can be delivered to the user breathing interface after being humidified by the humidifier.

3. The breathing assistance apparatus of claim 1, wherein the scrolling text comprises a series of images that provides an appearance of textual information scrolling or moving on the first portion of the display screen.

4. The breathing assistance apparatus of claim 1, wherein the display screen comprises a coloured background different from, or contrasting with, a colour of the scrolling text, the coloured background surrounding the scrolling text on the first portion of the display screen and/or one of the coloured background and the colour of the scrolling text on the first portion of the display screen are the same colour as the animation on the third portion of the display screen.

5. The breathing assistance apparatus of claim 1, wherein the first portion of the display screen comprises at least one flashing element to indicate an urgent message or an alarm.

6. The breathing assistance apparatus of claim 1, wherein the scrolling text on the first portion of the display screen and/or the animation on the second third portion of the display screen may be altered in response to a user input and/or a triggering event and wherein only one of the scrolling text on the first portion of the display screen and the animation on the third portion of the display screen does not change in response to the user input and/or the triggering event.

7. The breathing assistance apparatus of claim 1, wherein the animation on the third portion of the display screen comprise information indicative of operating parameters of the breathing assistance apparatus, settings of the breathing assistance apparatus, and/or conditions of the breathing assistance apparatus and wherein the animation on the third portion of the display screen are changed by the controller in response to changes in measured operating parameters, changes in operational modes, user input, and/or triggering events.

8. The breathing assistance apparatus of claim 1, wherein the animation on the third portion of the display screen comprises an animated fan.

9. A breathing assistance apparatus comprising:
a controller operable to control at least one aspect of operation of the breathing assistance apparatus;
a single housing including a flow generator and a humidifier disposed within the single housing, the flow generator operative to create a flow of breathing gases, the flow generator in fluid communication with the humidifier and upstream of the humidifier; the humidifier in fluid communication with the flow generator and operative to humidify the flow of breathing gases; wherein the humidifier is controlled by the controller, the single housing including an organic light emitting diode display screen and one or more buttons adjacent the display screen, the display screen and the one or more buttons located on an upper side of the housing, such that the display screen is easily visible when the breathing assistance apparatus is in an operative position;
the display screen adapted to provide visual information regarding the breathing assistance apparatus to a user, the display screen comprising a first portion, a second portion, and a third portion, the first portion of the display screen configured to display scrolling text along the lower portion of the display screen, the second portion of the display screen configured to display dynamic information comprising a countdown timer, and a third portion of the display configured to display an animation comprising a moving icon indicative of a current operational mode that visually illustrates to a user that the current operational mode is active, wherein during the current operational mode, the scrolling text providing textual information that is related to the animation changes and the countdown timer changes while the animation remains unchanged, the scrolling text being displayable in conjunction with the animation, wherein the scrolling text is indicative of instructions, a warning, a fault condition or an event of the breathing assistance apparatus, wherein the breathing assistance apparatus is configured to prompt the user to perform maintenance tasks and troubleshooting through the display screen.

10. The breathing assistance apparatus of claim 9, further comprising an inspiratory conduit and a user breathing interface, the inspiratory conduit being in fluid communication with the humidifier and the user breathing interface such that the flow of breathing gases can be delivered to the user breathing interface after being humidified by the humidifier.

11. The breathing assistance apparatus of claim 9, wherein the scrolling text comprises a series of images that provides an appearance of textual information scrolling or moving on the first portion of the display screen.

12. The breathing assistance apparatus of claim 9, wherein the display screen comprises a coloured background different from, or contrasting with, a colour of the scrolling text, the coloured background surrounding the scrolling text on the first portion of the display screen and/or one of the coloured background and the colour of the scrolling text on the first portion of the display screen are the same colour as the animation on the third portion of the display screen.

13. The breathing assistance apparatus of claim 9, wherein the first portion of the display screen comprises at least one flashing element to indicate an urgent message or an alarm.

14. The breathing assistance apparatus of claim 9, wherein the scrolling text on the first portion of the display screen and/or the animation on the third portion of the display screen may be altered in response to a user input and/or a triggering event and wherein only one of the scrolling text on the first portion of the display screen and the animation on the second portion of the display screen does not change in response to the user input and/or the triggering event.

15. The breathing assistance apparatus of claim 9, wherein the animation on the third portion of the display screen comprise information indicative of operating parameters of the breathing assistance apparatus, settings of the breathing assistance apparatus, and/or conditions of the breathing assistance apparatus and wherein the animation on the third portion of the display screen are changed by the controller in response to changes in measured operating parameters, changes in operational modes, user input, and/or triggering events.

16. The breathing assistance apparatus of claim 9, wherein the animation on the third portion of the display screen comprises an animated fan.

\* \* \* \* \*

UNITED STATES PATENT AND TRADEMARK OFFICE
CERTIFICATE OF CORRECTION

| | |
|---|---|
| PATENT NO. | : 11,000,666 B2 |
| APPLICATION NO. | : 14/899500 |
| DATED | : May 11, 2021 |
| INVENTOR(S) | : Christopher Malcolm Crone et al. |

It is certified that error appears in the above-identified patent and that said Letters Patent is hereby corrected as shown below:

In the Claims

In Column 11, Claim 1, Line 56, delete "apparatus" and insert --apparatus,--.

In Column 12, Claim 6, Line 16, delete "second third" and insert --third--.

In Column 12, Claim 9, Line 43, delete "humidifier;" and insert --humidifier,--.

In Column 12, Claim 9, Line 45, delete "gases;" and insert --gases,--.

Signed and Sealed this
Fifth Day of October, 2021

Drew Hirshfeld
*Performing the Functions and Duties of the*
*Under Secretary of Commerce for Intellectual Property and*
*Director of the United States Patent and Trademark Office*